United States Patent [19]

Kato et al.

[11] Patent Number: 4,780,079

[45] Date of Patent: Oct. 25, 1988

[54] TOOTH ARTICULATOR FOR USE IN CORRECTING TOOTH OCCLUSAL DISHARMONY

[75] Inventors: Isamu Kato, Toyonaka; Sadayuki Yuhda, Suita; Naoki Oda, Nishinomiya; Masahiro Suganuma, Suita, all of Japan

[73] Assignee: Sankin Kogyo Kabushiki Kaisha, Osaka, Japan

[21] Appl. No.: 900,081

[22] Filed: Aug. 25, 1986

[30] Foreign Application Priority Data

Aug. 30, 1985 [JP] Japan ................................. 60-192274

[51] Int. Cl.$^4$ ............................................... A01C 7/00
[52] U.S. Cl. ..................................... 433/2; 433/199.1; 433/202.1; 433/207
[58] Field of Search ..................... 433/2, 217.1, 199; 428/670, 672, 673, 668, 680, 613, 935; 427/2

[56] References Cited

U.S. PATENT DOCUMENTS

| | | | |
|---|---|---|---|
| 856,034 | 6/1907 | Crouse | 106/35 |
| 2,206,502 | 9/1935 | Heligman | 106/35 |
| 4,324,630 | 4/1982 | Sugitz et al. | 433/217.1 |
| 4,427,501 | 1/1984 | Rogers | 433/217.1 |

*Primary Examiner*—Robert Peshock
*Attorney, Agent, or Firm*—Oblon, Fisher, Spivak, McClelland & Maier

[57] ABSTRACT

A tooth articulator for use in correcting tooth occlusal disharmony or interference, the articulator keeping the mouth hygienic irrespective of a long period of use in the mouth by utilizing the antibiotic power of the cobalt coating wholly or partly covering the surface of the base material of the articulator.

10 Claims, No Drawings

TOOTH ARTICULATOR FOR USE IN CORRECTING TOOTH OCCLUSAL DISHARMONY

BACKGROUND OF THE INVENTION

1. Field of the Invention

The present invention relates to a tooth articulator for use in correcting tooth occlusal disharmony, and more particularly to a tooth articulator for such use, the articulator keeping the mouth hygienic by utilizing the antibiotic power of Co ions ($Co^{2+}$).

2. Description of the Prior Art

Besides the care of decayed teeth it is important to eliminate occlusal interference, which is responsible for the unclean mouth. In correcting occlusal disharmony a tooth articulator, such as a mouth bracket or ring, is used. However such artificial tools placed on or between the teeth are likely to provide beds for germs to grow in the mouth, and spoil the mouth hygiene. Particularly when the tooth dentition is to be restored over a year or more with the use of an articulator, it continues to be kept on the tooth (teeth) for the same long time, which provides a bed for streptococcus mutans and other bacteria to grow. These bacteria decay teeth, and produce cavities.

Therefore double cares will be required; that is, the second care is about eliminating the cavities subsequent to the first care; that is, the tooth dentition is restored. As a result even though the occlusal disharmony is corrected the tooth surfaces remains unclean. If the teeth are too much decayed it may be required to use tooth inlays, which is painful and costly for the patient.

OBJECTS AND SUMMARY OF THE INVENTION

The present invention aims at solving the problems pointed out above, and has for its object to provide an improved tooth articulator keeping the mouth hygienic regardless of a long period of use on the tooth.

Other objects and advantages of the present invention will become more apparent from the following description when taken in conjunction with the example obtained from the experiments.

According to the present invention there is provided a tooth articulator keeping the mouth hygienic, the articulator comprising a base material and a Co coating film covering the base material.

The present invention is based on the discovery and has been embodied as a result of experiments:

In order to test the antibiotic performance of metals Au, Ni, Cr, Co, Ag, Cu and Fe were tested by using a culture bed in which streptococcus mutans, trichophyton, candida arbicans and candida tropicalis were grown. As a result it has been clearly found that Cu, Co, Au and Fe have an antibiotic power derived from the elution of their ions into the culture bed. However the Cu ion, Au ion, and Fe ion involve problems; that is, the Cu ion has larger antibiotic power than the other two ions but tends to oxidize under the wet atmosphere in the mouth, thereby blackening the tooth surfaces. In addition the Cu ion is harmful, so that copper cannot be applied to the articulator used in the mouth. This disadvantage will trade off its superior antibiotic performance. Fe ion also tends to oxidize in the presence of water, such as saliva, in the mouth. However the Fe ion has a weaker antibiotic power than Cu ion. Gold also has a weaker antibiotic power to be used for antiseptic purpose, particularly where a strong germ-killing performance is required for keeping the mouth hygienic.

In contrast, Co ion exhibits a superior antibiotic, next to the Cu ion, and more advantageously it has no tendency of becoming oxidized and blackened. In addition it is not harmful, and cobalt is a strong metal to be used as an articulator in the mouth.

DETAILED DESCRIPTION OF THE PREFERRED EMBODIMENT

Under the present invention a tooth articulator is covered with a Co film in such a condition so as to permit the cobalt ions to elude into saliva in the mouth.

A typical method of forming the film is electroplating but the methods are not limited to it, on condition that an enough amount of Co ion can be eluted so as to kill the bacteria in and around the teeth. If an adequate amount of elution is expected, it is not necessary to cover the entire surface of the articulator with the Co film.

In general if the amount of Co elution is in excess, the Co ions are nevertheless harmful to the human health. However the experiments have revealed that the elution of Co ions into saliva is too small to be worried about the harm to the human health. This discovery is supported by a clynical experiment in which Co ion had been dosed to a child at the rate of 100 mg/day for seven months without any problem. ("TOXICOLOGY" by Yamadaet al, July 1, 1976, and "INDUSTRIAL TOXICOLOGY HANDBOOK" BY Mitsuru Goto et al, Oct. 28, 1977)

It sometimes happens that the film peels off when particular kinds of materials are used for the articulator; for example, when it is made of stainless steel or various Ni-Cr steels. But under the present invention there is no worry about the selection of the material used for the articulator. For safety purpose it is possible to provide an intermediate layer of Ni or Cu, which is also made by electroplating.

It is possible to cover the Co film with a second layer of Au, Ag, Pd, Rh, Pt, Ir, Ni, Sn or their alloy for ornamental purpose and/or anti-corrosion purpose. However if the Co film is completely sealed with the second layer the elution becomes impossible. To avoid this problem care must be taken how to decide the size and number of pores produced in the second layer and the thickness thereof. When the second layer is provided with a large number of pores the second layer can be made of base metals, such as In or Cr.

The antibiotic power of the Co film will be demonstrated by the the Example:

A Co-plated stainless steel disc (1 mm and 10 mm diameter) was placed on a culture bed of gelatin in which a microorganism, such as streptococcus mutans KIR, IBBHT, FAI, or OHZ176, were cultured, and a sterility range (sterility circle) on the disc was observed.

As a result a sterility circle of 25 mm diameter from the center of the disc was found.

The disc was coated with second layers of Cr, one having a thickness of 1 $\mu$m, and the other having a thickness of 3 $\mu$m, The resulting sterility circle in the first case was 20 mm diameter, and that of the second case was 13 mm diameter from the center of the disc. The disc of the first case was tested with respect to candida arbicans and candida tropicalis. The sterility circle was 20 mm diameter from the center of the disc.

A Co-plated seamless ring of stainless steel usable as a tooth articulator was placed on the gelatin bed mentioned above, and the ferility circle of the same size as that mentioned above was observed around the ring.

What is claimed is:

1. An orthodontic fitting suitable for correcting occlusal disharmony, consisting essentially of a base material and a coating of Co overlaid on said base material, thereby being capable of killing bacteria in the vicinity of said fitting, which orthodonic fitting further comprises an intermediate layer of Ni between the coating of Co and the base material.

2. The orthodontic fitting of claim 1, which further comprises an intermediate layer of Cu between the coating of Co and the base material.

3. An orthodonic fitting suitable for correcting occlusal disharmony, consisting essentially of a base material and a coating of Co overlaid on said base material, thereby being capable of killing bacteria in the vicinity of said fitting, which orthodonic fitting further comprises an intermediate layer of Cu between the coating of Co and the base material.

4. An orthodonic fitting suitable for correcting occlusal disharmony, consisting essentially of a base material and a coating of Co overlaid on said base material, thereby being capable of killing bacteria in the vicinity of said fitting, which orthodonic fitting further comprises an outer porous plated layer.

5. The orthodontic fitting of claim 4, wherein the intermediate layer is produced by electroplating.

6. The orthodontic fitting of claim 4, wherein said outer plated layer comprises one or more metals which are noble with respect to Co.

7. The orthodontic fitting of claim 4, wherein the porous plated layer comprises a metal selected from the group consisting of Au, Ag, Pd, Rh, Pt, Ir, Ni, Sn and alloys thereof.

8. The orthodontic fitting of claim 4, wherein the porous plated layer comprises one or more base metals.

9. The orthodontic fitting of claim 4, wherein the porous plated layer comprises a metal selected from the group consisting of In, Cr and an alloy thereof.

10. The orthodontic fitting of claim 4, wherein the porous plated layer has a thickness of 5 micrometers or less.

* * * * *